US00PP29435P3

(12) United States Plant Patent
Warner

(10) Patent No.: US PP29,435 P3
(45) Date of Patent: Jul. 3, 2018

(54) CLIMBING ROSE PLANT NAMED 'CHEWESIC'

(50) Latin Name: *Rosa hybrida*
Varietal Denomination: CHEwesic

(71) Applicant: Early Morning LLC, Lawrenceburg, IN (US)

(72) Inventor: Christopher Hugh Warner, Shropshire (GB)

(73) Assignee: Early Morning, LLC, Pomona, CA (US)

( * ) Notice: Subject to any disclaimer, the term of this patent is extended or adjusted under 35 U.S.C. 154(b) by 250 days.

(21) Appl. No.: 14/757,147

(22) Filed: Nov. 25, 2015

(65) Prior Publication Data

US 2017/0150662 P1 May 25, 2017

(51) Int. Cl.
*A01H 5/02* (2018.01)

(52) U.S. Cl.
USPC ..... Plt./113
CPC ..... *A01H 5/0222* (2013.01)

(58) Field of Classification Search
USPC ..... Plt./113, 112
CPC ..... A01H 5/0222
See application file for complete search history.

(56) References Cited

PUBLICATIONS http://witherspoonroseculture.blogspot.com/2014/10/2015-rose-introduction.html; Oct. 3, 2014; 8 pages.*
2015 Weeks Roses 2015 Wholesale Rose Catalog, 84 pages, Jan. 1, 2016.

* cited by examiner

*Primary Examiner* — Kent L Bell
(74) *Attorney, Agent, or Firm* — McKee, Voorhees & Sease, PLC

(57) ABSTRACT

A new variety of Climbing rose suitable for garden decoration, having flowers of salmon orange coloration.

1 Drawing Sheet

Classification: The present invention relates to a new *Rosa hybrida* plant.

Variety denomination: The new plant has the varietal denomination 'CHEwesic'.

BACKGROUND OF THE INVENTION

This invention relates to a new and distinct variety of Climbing Rose. It has as its seed parent the variety known as 'KORwest' (not patented) and as its pollen parent the variety known as 'DICmagic' (not patented).

SUMMARY OF THE INVENTION

Among the features which distinguish the new variety from other presently available and commercial rose cultivars known to the inventor are the following combinations of characteristics: its numerous stipitate glands on the peduncle, its excellent color stability throughout the life of the flower, its very vigorous growth and its many stipitate glands on the new shoots and branches. The plant has a spreading climbing growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'CHEwesic' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'KORwest' by the following combination of characteristics: whereas 'CHEwesic' bears double flowers (about 23 to 38 petals) of salmon orange coloration, 'KORwest' bears double flowers of apricot orange coloration with lesser petalage (about 20 to 30 petals). The new variety has a moderate fruity fragrance, whereas the seed parent has a strong spice and rose fragrance.

The new variety may be distinguished from its pollen parent, 'DICmagic' by the following combination of characteristics: whereas 'CHEwesic' bears double flowers (about 23 to 38 petals) of salmon orange coloration, 'DICmagic' bears double flowers of orange blend coloration with significantly lesser petalage (about 25 petals). The new variety is classified as a Climbing rose with a spreading climbing growing habit with canes about 300 cm. to about 350 cm. in length, whereas the pollen parent is classified as a Miniature rose with a more compact significantly shorter growing habit (about 35 to about 75 cm. in height).

COMPARISON WITH THE CLOSEST COMMERCIALLY AVAILABLE CULTIVAR

The closest commercially available cultivar to the new variety is the seed parent 'KORwest' (not patented).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Pomona, Calif. in the month of November.

Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of November. Phenotypic expression may vary with environmental, cultural and climatic conditions, as well as differences in conditions of light and soil.

FLOWER

The new variety sometimes bears its flowers singly, usually in clusters of three to twenty seven or more per stem. Flowers may be borne in regular rounded clusters on strong short to long stems (about 18 to about 240 cm.). The cluster ranges from about 16 to about 23 cm. in diameter. Outdoors, the plant blooms abundantly and nearly continuously during the growing season. The flowers have a moderate fruity fragrance.

BUD

The peduncle is about 1.2 to about 4.8 cm. in length, of average to somewhat heavy caliper (about 0.2 to about 0.3 cm. in diameter), and usually erect to sometimes bending. It is moderately rough, with numerous stipitate glands and some hairs. Peduncle color is between 146C and 146B sometimes lightly suffused, especially on the side exposed to the sun, with between 187B and 183A.

Before the calyx breaks, the bud is about 1.1 to about 1.6 cm. in diameter at the widest point, about 1.1 to about 1.8 cm. in length, ovoid to somewhat globular in shape. The surface of the bud bears between 4 to 6 foliaceous appendages with many stipitate glands and some hairs, usually with slender entire foliaceous parts extending beyond the tip of the bud about ¼ or more of its length. Bud color is between 146B and 146A often heavily suffused, especially on the side exposed to the sun, with between 187B and 187A.

The sepals are about 1.4 to about 2.8 cm. in length and about 0.6 to about 1.0 cm. in width at the widest point. The outer surface color of the sepal is between 146B and 146A often heavily suffused, especially on the side exposed to the sun, with between 187B and 187A. The outer surface of the sepal is moderately rough and bears between 0 to 2 foliaceous appendages with many stipitate glands and some hairs. The inner surface color of the sepal is near 146C broadly bordered by near 137A. After the sepals open, the inner surface color is often heavily suffused, especially on the area exposed to the sun, with between 187B and 187A. The inner surface of the sepal is covered with fine wooly tomentum; sepal margins are lined with many stipitate glands and hairs.

The receptacle of the flower is of medium length (about 0.3 to about 0.7 cm.) and somewhat heavy in caliper (about 0.6 to about 0.9 cm. in diameter). The receptacle is cup-shaped in form. Its surface is smooth with few hairs but somewhat rough at the base with few stipitate glands and with moderately thick fleshy walls. The receptacle color is between 144A and 146A sometimes heavily suffused, especially on the side exposed to the sun, with between 187B and 187A.

As the petals open (after the calyx breaks), the bud is about 1.4 to about 2.4 cm. in diameter at the widest point, about 1.3 to about 2.8 cm. in length, and globular to somewhat ovoid in form. The color of the under surfaces of the newly opened petals is between 32B and 31A. At the point where the petal attaches, there is a large zone of between 11A and 10A. The color of the upper surfaces of the newly opened petals is between 33B and 28B. At the point where the petal attaches, there is a large zone of between 12B and 12A.

BLOOM

When fully open, the bloom ranges from about 6.1 to about 10.4 cm. in diameter. Petalage is double with about 23 to 38 petals and about 2 to 7 petaloids irregularly arranged. When partially open, the bloom form is moderately globular to cupped, and the petals are somewhat tightly spiraled to cupped with petal edges somewhat reflexed outward. When fully open, the bloom form is more cupped, and the petals are loosely cupped to moderately undulated with petal edges moderately reflexed outward to sometimes somewhat reflexed inward.

PETALS

The substance of the petals is somewhat heavy and of moderately thin thickness, with upper surfaces satiny and under surfaces slightly shiny. The petals are about 1.8 to about 4.1 cm. in length and about 1.5 to about 3.8 cm. in width at the widest point. Petal margins are entire.

The outer petals are nearly rounded to somewhat obovate in shape with rounded apices.

The inner petals are broadly obovate in shape with rounded apices.

Petaloids are about 0.9 to about 2.6 cm. in length and about 0.5 to about 1.3 cm. in width at the widest point. Petaloids are irregularly shaped moderately oblanceolate to somewhat subulate with rounded apices.

NEWLY OPENED FLOWER

The under surface color of the outer, intermediate and inner petals is between 33C and 30D. At the point where the petal attaches, there is a large zone of between 11B and 10B. The upper surface color of the outer, intermediate and inner petals is between 32B and 30D. At the point where the petal attaches, there is a large zone of near 12B.

The under and upper surface colors of the petaloids are similar in coloration to the upper and under surfaces of the intermediate and inner petals.

The general tonality of the newly opened flower is between 32B and 30D.

THREE-DAY-OLD FLOWER

The under surface color of the outer, intermediate and inner petals is between 32D and 37B. At the point where the petal attaches, there is a large zone of between 4C and 5D. The upper surface color of the outer, intermediate and inner petals is between 41C and 37B. At the point where the petal attaches, there is a large zone of near 10B.

The under and upper surface colors of the petaloids are similar in coloration to the upper and under surfaces of the intermediate and inner petals.

The general tonality of the three-day-old flower is between 41C and 37B.

On the spent bloom, the petals usually drop off cleanly.

In November in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 155) and are arranged regularly about the pistils; a few are mixed with petaloids or tucked in the calyx. The filaments are of medium to somewhat long length (about 0.5 to about 1.2 cm.) most with anthers. Filaments are between 11A and 8A in color sometimes lightly suffused with near 53C. The anthers are of medium size to somewhat small for the class and all open approximately at the same time. Anther color when immature is near 22A on the external part and near 12D on the internal part. Anther color at maturity is near 163C on the external part and near 200A on the internal part. Pollen is moderate and between 23B and 21A in color.

FEMALE REPRODUCTIVE ORGANS

Pistils vary in number (average about 90). The styles are moderately even, somewhat short to average in length (about 0.3 to about 0.8 cm.), thin in caliper, and loosely bunched to somewhat separated. Stigma color is between 13C and 11A. Style color is between 150C and 154C often moderately suffused near the top with between 53B and 53C. Ovaries are usually all enclosed in the calyx. The ovaries are of medium size and between 159B and 159C in color.

Hips are of somewhat short to average length (about 1.1 to about 2.2 cm.), rounded in form with a flat top and a flat base, and near 34B in color when ripe. The hip surface is smooth with very thick fleshy walls. The sepals are moderately permanent and usually straight in shape.

The seeds are irregularly rounded, smooth in texture, approximately 15 to about 22 per hip, about 0.3 to about 0.6 cm. in diameter at the widest point and between 164C and 165C in color.

FOLIAGE

The compound leaves are usually comprised of three to seven leaflets and are borne abundantly. The seven-leaflet leaves are about 8.6 to about 19.7 cm. in length and about 6.3 to about 14.9 cm. in width at the widest point, leathery to somewhat crisp in texture on both sides, and glossy in finish on the upper side and slightly glossy to almost matte in finish on the under side. The leaves have a pinnate venation pattern. The terminal leaflets are about 3.4 to about 7.7 cm. in length and about 2.5 to about 5.5 cm. in width at the widest point, shaped somewhat oval to nearly rounded with acute to somewhat acuminate apices and rounded to somewhat acute bases. Their margins are usually simply serrate.

The upper surface color of the mature leaf is between 137A and 146A. The under surface color of the mature leaf is between 147B and 148B. The under and upper colors of the leaf veins on the mature leaf are similar in coloration to the upper and under surfaces colors of the mature leaf. The upper surface color of the young leaf is between 137B and 146C, sometimes lightly suffused with between 187B and 183A. The under surface color of the young leaf is between 146B and 146C, sometimes lightly suffused with between 187B and 183A. The under and upper colors of the leaf veins on the young leaf are similar in coloration to the upper and under surfaces colors of the young leaf.

The rachis is about 5.2 to about 12.0 cm. in length, about 0.1 to about 0.2 cm in width at the widest point and rough. The upper side is moderately grooved with some stipitate glands on the edges of the grooves. The under side of the rachis is rough with few stipitate glands and small prickles. The rachis color is near 146C on the under side and near 137B on the upper side, sometimes lightly suffused on the young leaves with between 187B and 183A.

The stipules are about 1.2 to about 2.3 cm. in length and moderately narrow (about 0.3 to about 0.6 cm.) with somewhat long straight points that usually turn out at an angle of more than 45 degrees. The under and upper surface color of the stipule is between 146A and 146B. The upper and under surfaces of the stipules are smooth in texture.

The petiole is rough. The upper side is moderately grooved with some stipitate glands on the edges of the grooves. The under side of the petiole is rough with few stipitate glands and small prickles. The petiole is about 0.7 to about 1.9 cm. in length and about 0.1 to about 0.2 cm in width at the widest point. The petiole color is near 146C on the under side and near 137B on the upper side, sometimes lightly suffused on the young leaves with between 187B and 183A.

The plant displays an above average degree of resistance to downy mildew (*Peronospora sparsa*) and rust (*Phragmidium* sp.) and an average degree of resistance to powdery mildew (*Sphaerotheca pannosa*) as compared to other commercial varieties grown under comparable conditions in Pomona, Calif. The plant's winter hardiness and drought/heat tolerance are yet to be determined.

GROWTH

The plant has a spreading climbing growing habit with canes about 300 cm. to about 350 cm. in length with very full branching. It displays very vigorous growth and the canes are of moderately heavy caliper for the class (about 2.3 to about 3.4 cm. in diameter at the widest point).

The color of the major stems is between 137C and 146B. The major stems are rough in texture and they bear some large prickles that are about 1.1 to about 1.6 cm. in length. The large prickles are almost straight to angled slightly downward with a moderately long somewhat broad oval base; prickle color is between 165C and 165B. The major stem bears many small prickles of similar shape and coloration.

The color of the branches is between 146A and 146B. The branches are rough in texture and they bear some large prickles which are of similar shape to the large prickles on the major stems. The prickles are about 0.5 to about 1.0 cm. in length. The prickle color is between 165C and 164C. The branches bear many small prickles of similar shape and coloration with many stipitate glands.

The color of the new shoots is between 144A and 146B sometimes lightly suffused with between 187B and 187A. The new shoots are rough in texture and they bear some large prickles which are of similar size and shape to the large prickles on the branches; prickle color is between 153A and 152D sometimes lightly suffused with near 187C. The shoots bear many small prickles of similar shape and coloration with many stipitate glands.

I claim:

1. A new and distinct Climbing rose plant of the variety substantially as described and illustrated herein.

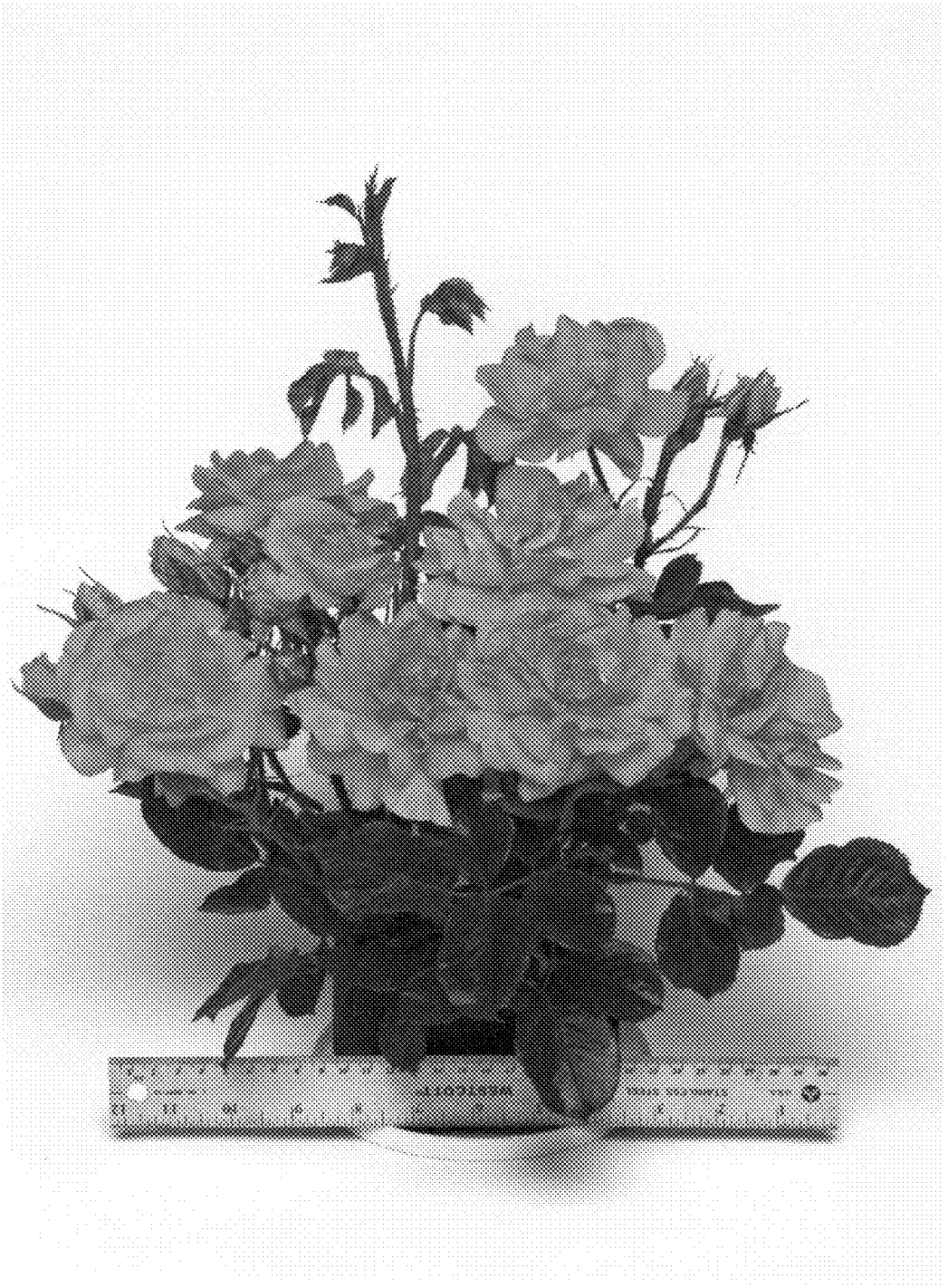

* * * * *